(12) United States Patent
Shrawat et al.

(10) Patent No.: US 9,403,785 B2
(45) Date of Patent: Aug. 2, 2016

(54) PROCESS FOR PREPARING AMORPHOUS CABAZITAXEL

(71) Applicant: SHILPA MEDICARE LIMITED, Raichur (IN)

(72) Inventors: Vimal Kumar Shrawat, Raichur (IN); Prashant Purohit, Raichur (IN); Rafiuddin Dr, Raichur (IN); Vinod Kumar Singh, Raichur (IN); Akshay Kant Chaturvedi, Raichur (IN)

(73) Assignee: SHILPA MEDICARE LIMITED, Karnataka (IN)

( * ) Notice: Subject to any disclaimer, the term of this patent is extended or adjusted under 35 U.S.C. 154(b) by 0 days.

(21) Appl. No.: 14/349,332

(22) PCT Filed: Dec. 26, 2012

(86) PCT No.: PCT/IN2012/000855
§ 371 (c)(1),
(2) Date: May 21, 2014

(87) PCT Pub. No.: WO2013/111157
PCT Pub. Date: Aug. 1, 2013

(65) Prior Publication Data
US 2014/0336246 A1 Nov. 13, 2014

(30) Foreign Application Priority Data
Jan. 3, 2012 (IN) .............................. 35/CHE/2012

(51) Int. Cl.
*C07D 305/14* (2006.01)
*C07D 413/12* (2006.01)

(52) U.S. Cl.
CPC ............ *C07D 305/14* (2013.01); *C07D 413/12* (2013.01)

(58) Field of Classification Search
CPC .................................................... C07D 305/14
USPC ...................................................... 549/510
See application file for complete search history.

(56) References Cited

U.S. PATENT DOCUMENTS

| | | | |
|---|---|---|---|
| 5,847,170 | A | 12/1998 | Bouchard et al. |
| 5,962,705 | A | 10/1999 | Didier et al. |
| 7,241,907 | B2 | 7/2007 | Didier et al. |
| 2011/0144362 | A1 | 6/2011 | Billot et al. |
| 2012/0149925 | A1 | 6/2012 | Kung et al. |
| 2012/0301425 | A1 | 11/2012 | Gupta |
| 2013/0109870 | A1* | 5/2013 | Lahiri et al. ................. 549/510 |
| 2014/0228426 | A1* | 8/2014 | Kung et al. ................... 514/449 |

FOREIGN PATENT DOCUMENTS

| | | |
|---|---|---|
| CN | 102285947 | 12/2011 |
| CN | 102336726 | 1/2012 |
| CN | 102532065 | 4/2012 |
| CN | 102675256 | 9/2012 |
| WO | 2005028462 | 3/2005 |
| WO | 2011051894 | 5/2011 |
| WO | WO 2011/051894 * | 5/2011 ........... A61K 31/164 |

OTHER PUBLICATIONS

John K. Haleblian. Characterization of habits and crystalline modification of solids and their pharmaceutical applications JournaPharm. Sci. 1975, 64(8), 1269-1288, pp. 20.

* cited by examiner

*Primary Examiner* — Erich Leeser

(57) ABSTRACT

The present invention provides a non-solvated amorphous form of (2α,5β,7β,10β,13α)-4-acetoxy-13-({(2R,3S)-3[ (tert-butoxy carbonyl) amino]-2-hydroxy-3-phenylpropanoyl}oxy)-1-hydroxy-7,10-dimethoxy-9-oxo-5,20-epoxytax-11-en-2-yl benzoate or Cabazitaxel (I),

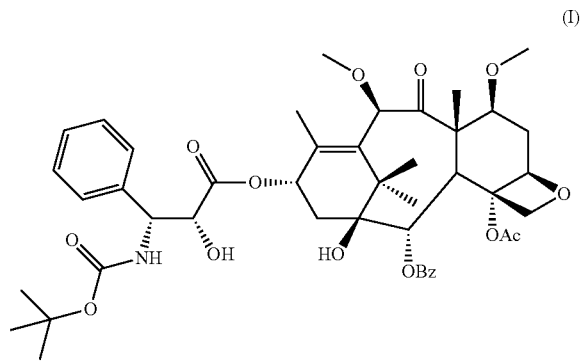

and process for preparation thereof.

The present application also provides a non-solvated amorphous form of (2α,5β,7β,10β,13α)-4-acetoxy-13-({(2R,3S)-3[ (tert-butoxy carbonyl) amino]-2-hydroxy-3-phenylpropanoyl}oxy)-1-hydroxy-7,10-dimethoxy-9-oxo-5,20-epoxytax-11-en-2-yl benzoate or Cabazitaxel (I) having an XRPD pattern as per FIG. 1, and IR spectrum as per FIG. 3 and is useful as an active pharmaceutical in a pharmaceutical composition comprising thereof and has anti-cancer activity.

9 Claims, 4 Drawing Sheets

PROCESS FOR PREPARING AMORPHOUS CABAZITAXEL

FIELD OF THE INVENTION

Particular aspects of the present application encompass the new solid form as amorphous form of Cabazitaxel and process for preparation thereof. Further, the present invention of this application also relates to pharmaceutical compositions comprising of non solvated amorphous form of Cabazitaxel which are useful in the treatment of various cancerous disorders.

BACKGROUND OF THE INVENTION

Cabazitaxel is chemically also known as (2α,5β,7β,10β,13α)-4-acetoxy-13-({(2R,3S)-3[(tert-butoxycarbonyl) amino]-2-hydroxy-3-phenylpropanoyl}oxy)-1-hydroxy-7,10-dimethoxy-9-oxo-5,20-epoxytax-11-en-2-yl benzoate (I).

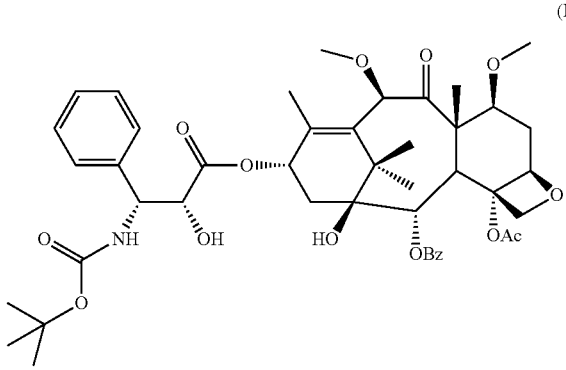

It is approved in USFDA as JEVTANA™ and is chemically mentioned in the label as (2α,5β,7β,10β,13α)-4-acetoxy-13-({(2R,3S)-3[(tert-butoxy-carbonyl) amino]-2-hydroxy-3-phenylpropanoyl}oxy)-1-hydroxy-7,10-dimethoxy-9-oxo-5,20-epoxytax-11-en-2-yl benzoate—propan-2-one (1:1) solvatomorph (Cabazitaxel:acetone). Cabazitaxel is a white to off-white crystalline powder and is lipophilic in nature, practically insoluble in water.

Bouchard et at in U.S. Pat. No. 5,847,170 provides the first disclosure of (2α,5β,7β,10β,13α)-4-acetoxy-13-({(2R,3S)-3[(tert-butoxy-carbonyl) amino]-2-hydroxy-3-phenylpropanoyl}oxy)-1-hydroxy-7,10-dimethoxy-9-oxo-5,20-epoxytax-11-en-2-yl benzoate (also known as Cabazitaxel), which also describes the process for preparing Cabazitaxel.

Kung Liang-Rern et at in U.S. 2012149925A1 disclose process for preparing Cabazitaxel by reacting beta-lactam side chain with a protected baccatin derivative in the presence of one or more Lewis acids and a base agent, wherein Lewis acid may be selected from LiBr, MgBr$_2$, CsBr, ZnBr$_2$, ZnCl$_2$, CuBr, Cu(CF$_3$SO$_4$)$_2$, BF$_3$.OEt$_2$, KBr, TiCl$_4$, SnCl$_2$, ScCl$_3$, VCl$_3$, AlCl$_3$, InCl$_3$, Al$_2$CO$_3$, CeCl$_3$, Ag$_2$O, ZnClO$_4$, LiClO$_4$, Ti{OCH(CH$_3$)$_2$}$_4$ or any combination thereof.

According to applicant of U.S. 20120149925A1, use of Lewis acid is one of inventive merit of the application. Applicant in the specification mentions that—comparing to the reaction carried out without Lewis acid, the presence of Lewis acid provides a more selective reaction, characterized by higher reaction rate, higher yield, more selective product, higher purity of the desired product and less side products.

Other disclosures related to Cabazitaxel process viz,—CN102532065A, CN102675256A and CN1023367268 also disclose similar processes however, either involving organometallic bases selected from n-BuLi, NaHMDS, KHMDS, KH & NaH and extremely low temperature conditions for the coupling reaction or different protecting groups on beta lactam side chains with varying bases and extremely low temperature conditions.

Subsequent to process of Cabazitaxel, the concern has remained for the solid form isolated for Cabazitaxel. As mentioned earlier, the Cabazitaxel form mentioned in the label as (2α,5β,7β,10β,13α)-4-acetoxy-13-({(2R,3S)-3[(tert-butoxy-carbonyl) amino]-2-hydroxy-3-phenylpropanoyl}oxy)-1-hydroxy-7,10-dimethoxy-9-oxo-5,20-epoxytax-11-en-2-yl benzoate—propan-2-one (1:1) solvatomorph (Cabazitaxel: acetone)is designated as Form-A in EMEA scientific discussion as well as in the subsequent patent U.S. Pat. No. 7,241,907.

Further, it appears from the literature that in order to achieve therapeutic role, it is Cabazitaxel base molecule that has to play the role and not necessarily its solvates as long as stable solvate or base form known to exists. In line with this, applicant in US 20120301425A1 (Eq. WO 2011051894A1) on page 2 mentions that Cabazitaxel may be administered in base form (cf. above formula), or in the form of a hydrate. It may also be a solvate, i.e. a molecular complex characterized by the incorporation of the crystallization solvent into the crystal of the molecule of the active principle (see in this respect page 1276 of J. Pharm. Sci. 1975, 64(8), 1269-1288). In particular, it may be an acetone solvate, and, more particularly, may be the solvate described in WO 2005/02846. It may be an acetone solvate of cabazitaxel containing between 5% and 8% and preferably between 5% and 7% by weight of acetone (% means content of acetone/content of acetone+cabazitaxel$^x$100). An average value of the acetone content is 7%, which approximately represents the acetone stoichiometry, which is 6.5% for a solvate containing one molecule of acetone.

Didier et al in U.S. Pat. No. 7,241,907 describes a crystalline form as acetone solvate of dimethoxy-docetaxel or 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate and its process for preparation by crystallization from an aqueous/acetone solution.

Billot Pascal et al in U.S. 20110144362 A1 appears to cover many crystalline forms, which include crystalline forms as anhydrides, solvates and ethanol hetero-solvates and hydrate forms of 4-acetoxy-2α-benzoyloxy-5β,20-epoxy-1-hydroxy-7β,10β-dimethoxy-9-oxotax-11-en-13α-yl (2R, 3S)-3-tert-butoxycarbonylamino-2-hydroxy-3-phenyl-propionate. The disclosure in this application provides nearly 11 new polymorphic forms-which include five (5) new crystal forms of Cabazitaxel anhydrous material designated as Form B, C, D, E, F, which are characterized by—Form B-DSC MP. 150° C., Form C-DSC MP. 146° C., Form D-DSC MP. 175° C., Form E-DSC MP. 157° C. and Form F-DSC MP. 148° C. along with their characteristic XRPD pattern.

U.S. 20110144362 A1 also disclosed four new crystal forms of ethanolate and heterosolvate of Cabazitaxel designated as Form B Ethanolate, Form D Ethanolate, Form E Ethanolate, and Form F Ethanolate/Water Heterosolvate.

Two New Hydrate Forms of Cabazitaxel which include Form C as Monohydrate and Form C as Dihydrate are also part of the disclosure. This patent specification also mentioned that only Form D anhydrous is highly stable, even more stable than acetone solvate form (Form A). This patent application further discloses that other solvates with solvents DCM/DIPE/nPA/IPA/Toluene/MIBK/THF/DMF etc.) were also prepared.

Perhaps polymorphism is known to be unique phenomenon in solid materials, wherein existence of different physical forms including shape, size, and arrangement of molecules in the physical state or polymorphs of same compound are known in the nature. A single compound, or a salt complex, may give rise to a variety of solids having distinct physical properties, which often results in 25. substantial differences in bioavailability, stability, and other differences between production lots of formulated pharmaceutical products. Due to this reason, since polymorphic forms can vary in their chemical and physical properties, regulatory authorities often require that efforts be made to identify all possible polymorphic forms, e.g., hydrate or anhydrate, crystalline or amorphous, solvated or un-solvated forms, etc. of the drug substances. However, the existence, and possible numbers, of polymorphic forms for a given compound cannot be predicted. In addition, there are no "standard" procedures that can be used to prepare different polymorphic forms of a substance. Further, it is often unclear for a chemical entity-whether any polymorphism exists in the molecule or not.

New forms of pharmaceutically active/useful compounds provide an opportunity to improve the drug performance characteristics of such product. Further, discovery of additional polymorphic forms may help in the identification of the polymorphic content of a batch of an active pharmaceutical ingredient. Therefore, there exists a need for preparing new forms of a drug substance and processes for preparation thereof.

Though the review of the above mentioned literature disclose diverse polymorphic crystalline forms and processes for the preparation of Cabazitaxel and its solvates, but due to one or more reasons most of them are not particularly convenient and amenable to industrial scale-up for preparing Cabazitaxel and its solvates. Thus, there is an apparent need of a new stable and usable form and its process for preparation, which may be cost-effective, industrially amenable and may overcome the drawbacks of various prior disclosed processes, e.g., multiple solvent combinations as well as multiple steps, which make these processes neither cost effective nor amenable to scale up for industrial scale production. According to the present invention there are provided non solvate amorphous form of Cabazitaxel and process for preparation thereof.

SUMMARY OF INVENTION

Particular aspects of the present specification relate to the non-solvate amorphous form of Cabazitaxel and process for preparation thereof.

In one aspect according to the present invention, the present invention provides non-solvated amorphous form of (2α,5β,7β,10β,13α)-4-acetoxy-13-({(2R,3S)-3[(tert-butoxy-carbonyl) amino]-2-hydroxy-3-phenylpropanoyl}oxy)-1-hydroxy-7,10-dimethoxy-9-oxo-5,20-epoxytax-11-en-2-yl benzoate or Cabazitaxel (I),

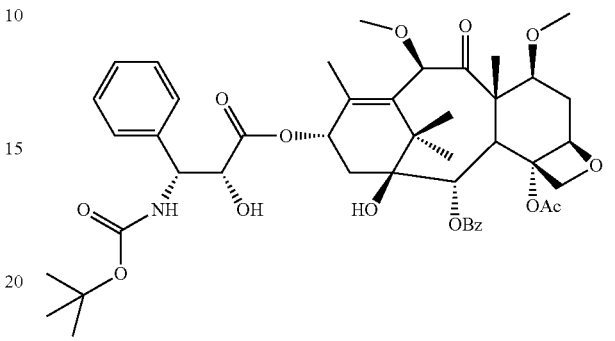

having up to 2% w/w or less of volatiles measured up to 160° C.

In another aspect, the present invention provides a process of preparation of non-solvated amorphous Cabazitaxel of formula (I) characterized by XRPD pattern as per FIG. 1, comprising the steps of— i) coupling of 7,10-Dimethoxy-10-deacetylbaccatin (7,10-Dimethoxy-10-DAB-III) (a) with 3-(tert-butoxycarbonyl)-2-(4-methoxyphenyl)-4-phenyloxazolidine-5-carboxylic acid (b) to yield coupled product (c) in the presence of carbodiimide coupling agent;

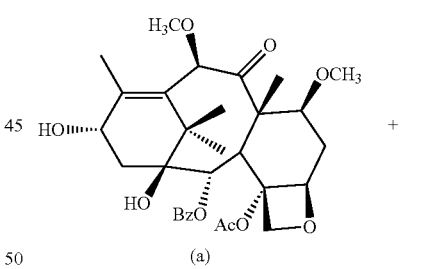

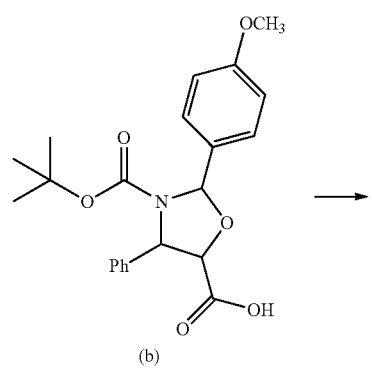

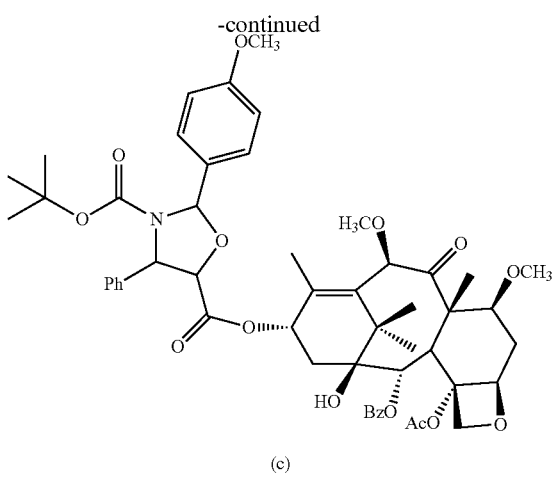

(c)

ii) ring opening of coupled product (c) in the presence of an organic acid to give crude Cabazitaxel (I);

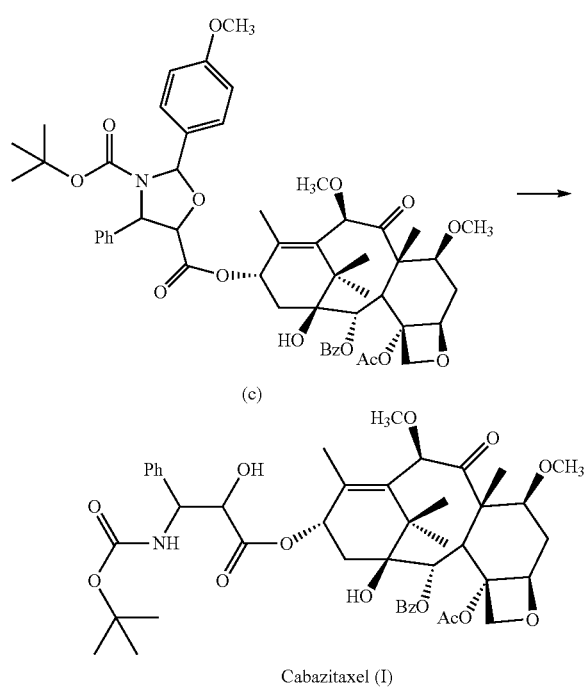

Cabazitaxel (I)

iii) optionally purifying the Cabazitaxel of step ii),
iv) combining Cabazitaxel or reaction material of step ii) or iii) with a polar organic solvent,
v) recovering the solvent,
vi) isolating the material as non-solvated amorphous Cabazitaxel.

In one particular aspect of the present invention, it also relates to a process for preparation of non-solvated amorphous Cabazitaxel wherein step v) of recovering the solvent is carried out under reduced pressure and at temperature ranging between 40° C-60° C.

In yet another aspect according to present application, it relates to a process for the preparation of non-solvated amorphous Cabazitaxel, from any known form of Cabazitaxel material, comprising the steps of— i) combining Cabazitaxel or its solvate or anhydrous crystalline form with a polar organic solvent selected from $C_1$-$C_3$ alcohol, 2-alkoxy ethanol or dimethylsulfoxide, ii) achieving dissolving of the reaction mass,
iii) recovering the solvent under reduced pressure and at temperature ranging between 40° C-60° C.,
iv) isolating the material as non-solvated amorphous Cabazitaxel.

In a further aspect, the present invention also relates to a composition comprising non-solvated amorphous Cabazitaxel of which at least 95%, by total weight of Cabazitaxel in the composition, is the amorphous form. The composition is substantially free of any other known forms of Cabazitaxel, its solvate or any other crystalline form.

In a further another aspect, it also relates to a pharmaceutical composition comprising non-solvated Cabazitaxel amorphous form of the present application and at least one or more pharmaceutically acceptable excipients.

Further particular aspects of the invention are detailed in the description part of the specification, wherever appropriate.

DETAILED DESCRIPTION

As set forth herein, embodiments of the present invention relate to non-solvated amorphous form of Cabazitaxel and process for preparation thereof.

In one embodiment of the present application, it provides non-solvated amorphous form of (2α,5β,7β,10β,13α)-4-acetoxy-13-({(2R,3S)-3[(tert-butoxy carbonyl) amino]-2-hydroxy-3-phenylpropanoyl}oxy)-1-hydroxy-7,10-dimethoxy-9-oxo-5,20-epoxytax-11-en-2-yl benzoate or Cabazitaxel (I),

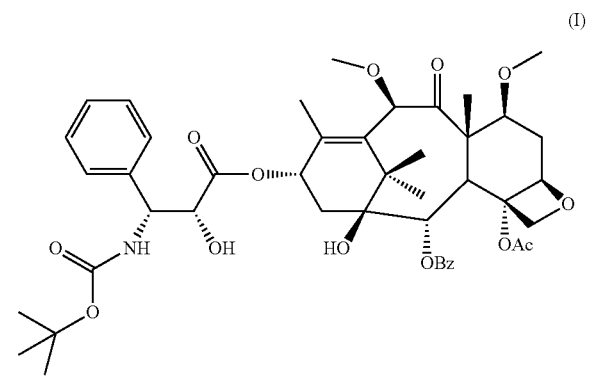

(I)

having up to 2% w/w or less of volatiles measured up to 160° C.

Figure 1:
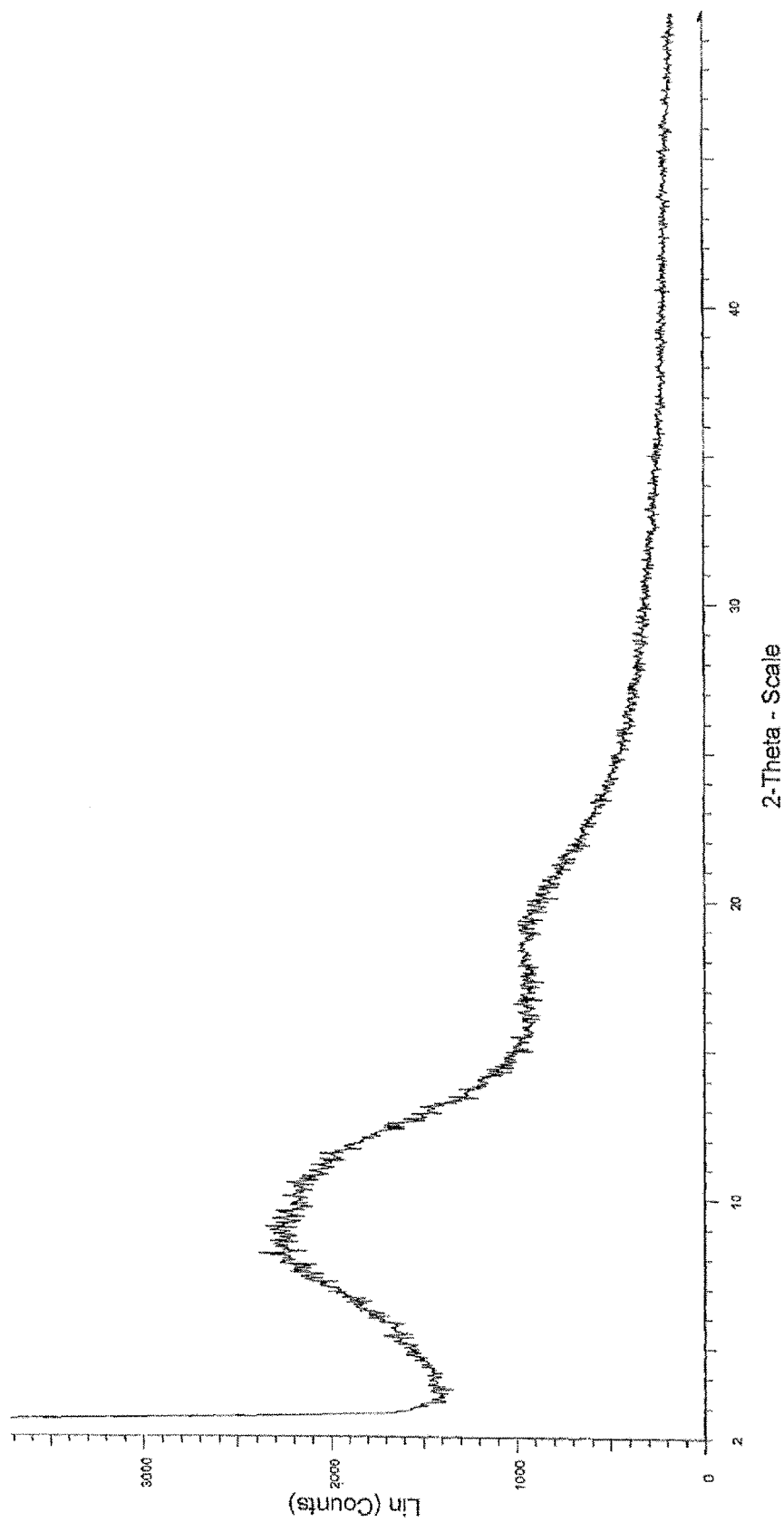
FIG. 1 is an example of X-ray powder diffraction ("XRPD") pattern of Cabazitaxel non-solvated amorphous form.

Substantially pure non-solvated amorphous form of Cabazitaxel exhibits an X-ray powder diffraction pattern substantially as shown in FIG. 1 indicating a solid form that lacks the long-range order (a characteristic of crystal) and having no pattern or structure.

The non solvated amorphous form of Cabazitaxel produced by the inventors of the present application is characterized by—
1. having up to 2% w/w or less of volatiles measured up to 160° C.;
2. having M. P. about 180° C. (melting starts from 176° C. and completed on 180° C.);
3. XRPD pattern similar to as shown in FIG. 1 and IR spectrum as per FIG. 3;
4. Mass spectrum showing two principal peaks at about [M+1]=836.8 and [M+NH$_4$+]=853.6

In another embodiment of the present application, it provides a process for preparation of non-solvated amorphous Cabazitaxel of formula (I)

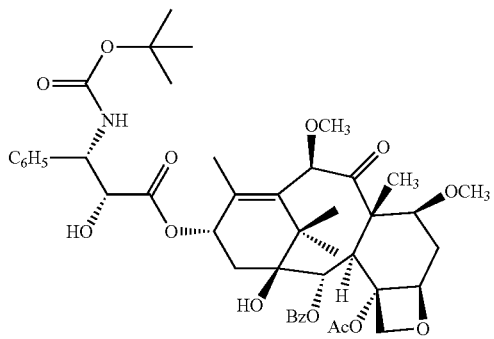

(I)

characterized by XRPD pattern as per FIG. 1, comprising the steps of—
i) coupling of 7,10-Dimethoxy-10-DAB-III (a) with 3-(tert-butoxycarbonyl)-2-(4-methoxyphenyl)-4-phenyloxazolidine-5-carboxylic acid (b) to yield coupled product (c) in the presence of carbodiimide coupling agent;

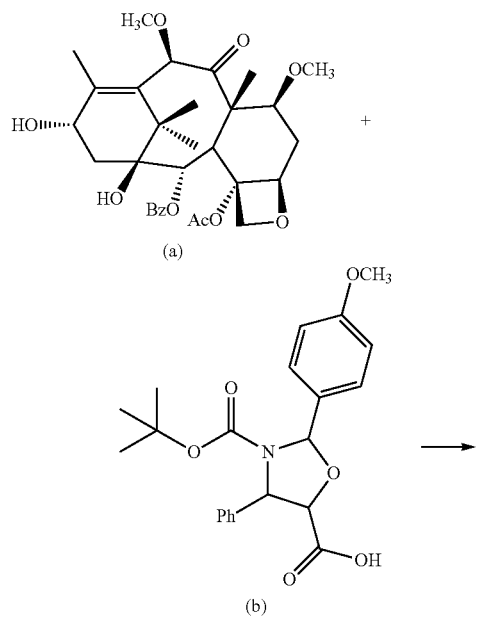

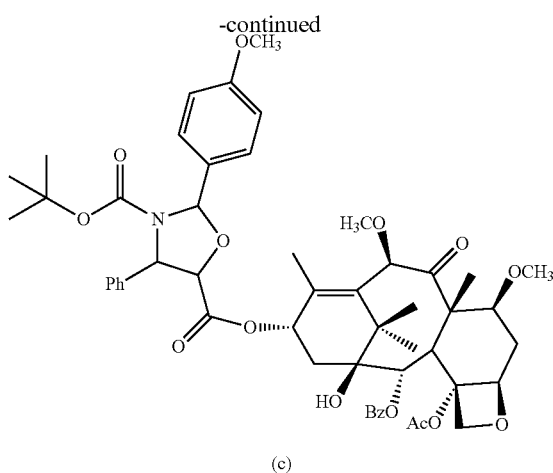

(c)

ii) ring opening of coupled product (c) in the presence of an organic acid to give crude Cabazitaxel (I);

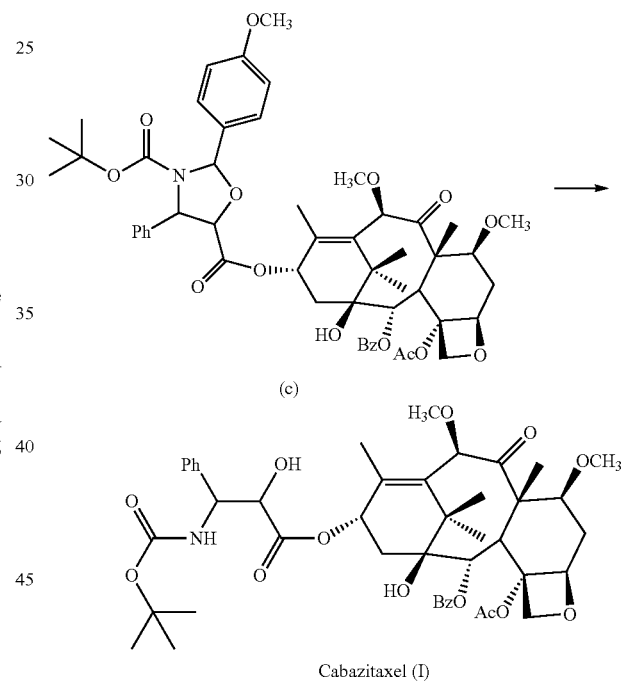

iii) optionally purifying the Cabazitaxel of step ii),
iv) combining Cabazitaxel or reaction material of step ii) or iii) with a polar organic solvent,
v) recovering the solvent,
vi) isolating the material as non-solvated amorphous Cabazitaxel.

The individual steps of the process according to the present invention for preparing non-solvated amorphous are detailed separately herein below.

Step i) comprising coupling of 7,10-Dimethoxy-10-DAB-III (a) with 3-(tert-butoxycarbonyl)-2-(4-methoxyphenyl)-4-phenyloxazolidine-5-carboxylic acid (b) to yield coupled product (c) in the presence of carbodiimide coupling agent.

7,10-dimethoxy-10-deacetylbaccatin (also known as 7,10-dimethoxy-10-DAB-III) and 3-(tert-butoxycarbonyl)-2-(4-methoxyphenyl)-4-phenyloxazolidine-5-carboxylic acid are reacted in an organic ester solvent at room temperature. Coupling reaction is done in the presence of carbodiimide as coupling agent and an organic base. Non limiting example of carbodiimide coupling agent include Dicyclohexyl carbodiimide (DCC), 1-ethyl-3-(3-dimethylaminopropyl)carbodiimide (EDC) etc. and organic base include 4,4-Dimethyl aminopyridine (DMAP), triethylamine (TEA), N-methyl morpholine (NMM), Diisopropyl ethyl amine (DIPEA) etc.

In a particular embodiment of the present application, involves the use of Dicyclohexyl carbodiimide (DCC) as carbodiimide coupling agent and organic ester solvent is ethyl acetate.

Step ii) ring opening of coupled product (c) in the presence of an organic acid to give crude Cabazitaxel (I)

Ring opening of Coupled product (c) side chain is performed in the presence of an organic acid.

The Coupled product (c) was dissolved in the organic solvent at room temperature (RT) under stirring to get the clear solution. The organic solvent used in the reaction includes but not limited to $C_{1-4}$ alcohol. The reaction mixture is cooled to 0° C., followed by addition of an organic acid. Non limiting examples of organic acid includes p-toluene sulfonic acid (PTSA) or organic aliphatic carboxylic acid (e.g. C2 to C5 carboxylic acid) or mono or di or tri halo substituted aliphatic carboxylic acid (e.g. mono or di or tri fluoro acetic acid and the like).

Step iii) optionally purifying the crude Cabazitaxel

The step of optionally purifying the Cabazitaxel comprises purification using column chromatography with eluent mixture comprising ethyl acetate and hexane in a appropriate proportion to achieve the purity of greater than 90% (area %) by HPLC. If required, a further purification step may also be performed by using re-dissolution in acetone followed by addition of n-hexane to get material having purity greater than 98% (area %) by HPLC.

Step iv) combining Cabazitaxel or reaction material of step ii) or iii) with a polar organic solvent Process of combining the Cabazitaxel with polar solvent may be carried out at room temperature (20-30° C.) or little higher temperature.

Cooling may be performed optionally for the combined mixture in order to control the product specifications in compliance to ICH requirement for impurity profiles, however, if the product obtained from Step iii) was already passed through column purification or subsequent purification, the reaction may be proceeded without cooling requirements. A slow cooling up to less than 15° C. but more than 5° C. is preferred in one of the embodiments according to the present application. A fast cooling rate of more than 10° C/min may be avoided in view of any probable inconsistency in the further steps.

The polar organic solvent according to the present invention are selected from methanol or 2-alkoxy ethanol or dimethylsulfoxide. In 2-alkoxy ethanol, alkyl group is selected from C1 to C3 alkyl.

The solution is prepared by combining Cabazitaxel with polar solvent up to the range between 50 to 90 times by weight of Cabazitaxel. In a particular embodiment, 310 mg of Cabazitaxel was combined with 25 mL of methanol (~80 times by weight of Cabazitaxel).

Combining the polar solvent with Cabazitaxel is followed up by achieving dissolving of the reaction mass.

Any Cabazitaxel—whether obtained in step ii), or purified Cabazitaxel isolated from step iii), reaction mass of step ii) or iii) without isolation of Cabazitaxel, or any known form of Cabazitaxel material may be used for combining and preparing the solution.

A solution of Cabazitaxel in a polar organic solvent comprise addition of solvent in lot wise portions of two to four lots at a time interval of 10 to 30 mins, however, it may be added in continuous ways also, with slow addition rate followed by continuous stirring. In one of the preferred embodiment, the time interval used was 10 minutes for two lots of solvent addition while maintaining the stirring. Solvent addition was carried out at a temperature of not more than 30° C.

The combined mixture may be maintained for about 1-5 hrs, however, this time may be more, depending upon achieving the desired solution nature more particularly and preferably a clear solution and equilibration to impurity profile compliance. The equilibration process may involve repetition of the solution forming process followed by drying in the same polar solvent to achieve the purity of the active component.

The process related impurities, including unreacted intermediates, side products, degradation products and other medium dependent impurities, that appear in the impurity profile of the Cabazitaxel may be substantially removed by the process of the present invention resulting in the formation non solvated amorphous form. In view of maintaining the equilibrium to the impurity profile compliance, the process may require in-process quality checks to avoid unnecessary repetitions of the same process step.

Wherever required, the solution may be subjected to filtration to achieve the clear solution and the same clear solution may be treated with charcoal or activated carbon to get impurities levels further controlled and later on subjected to next step.

Step v) recovering the solvent.

The process involves recovering the solvent under reduced pressure at temperature ranging between 40C-60° C. Reduced pressure conditions may be suitably utilized by person skilled in the art in order to recover the solvent in the reaction mass to achieve the dried material.

The merit of the process according to the present invention resides in that—product obtained after recovery is obtained in non-solvated amorphous form of Cabazitaxel. Said material was found devoid of any crystal lattice and adequately stable to handle and store for longer time (at least up to more than 6 months) without any significant or measurable change in its morphology and physicochemical characteristics.

Step vi) isolating the material as non-solvated amorphous Cabazitaxel.

Process of isolating non solvated amorphous form of Cabazitaxel comprise processes but not limited to conventional processes including scrapping, if required filtering from slurry and optional drying, which may be carried out at room temperature for the suitable durations to retain the amorphous form characteristics.

In another embodiment of the present invention, it provides process for preparing non-solvated amorphous Cabazitaxel, wherein the recovering the solvent is carried out under reduced pressure and at temperature ranging between 40° C-60° C. in any reaction mixtures comprising Cabazitaxel in polar organic solvent. Reduced pressure (vacuum) conditions may be suitably utilized by person skilled in the art in order to recover the solvent in the reaction mass to achieve the dried material. The product obtained after recovery is obtained in non-solvated amorphous form of Cabazitaxel. Said material can be stored for longer time (at least up to more than 6 months) without any significant or measurable change in its morphology and physicochemical characteristics.

In a further another embodiment, the present invention provides process for the preparation of non-solvated amorphous Cabazitaxel, from any known form of Cabazitaxel material, comprising the steps of— i) combining Cabazitaxel or its solvate or anhydrous crystalline form with a polar organic solvent selected from C1-C3 alcohol, 2-alkoxy ethanol or dimethylsulfoxide,
ii) achieving dissolving of the reaction mass,
iii) recovering the solvent under reduced pressure and at temperature ranging between 40° C-60° C.,
iv) isolating the material as non-solvated amorphous Cabazitaxel.

In this embodiments of the present invention of process for the preparation of non-solvated amorphous Cabazitaxel, any Cabazitaxel or its solvate or anhydrous crystalline form or any of its less stable form or impure form obtained from any source or by any of the processes known in the prior art may be utilized to result directly the non-solvated amorphous Cabazitaxel of the present invention.

The remaining steps of the embodiment shall be construed in line with the earlier detailed embodiment.

Substantially pure non solvated amorphous form of Cabazitaxel obtained according to the process of the present invention results in the final API purity by HPLC of more than 99% w/w.

The non-solvated amorphous form of Cabazitaxel described herein may be characterized by X-ray powder diffraction pattern (XRPD) and Thermal techniques such as differential scanning calorimetry (DSC) analysis. The samples of non-solvated amorphous form of Cabazitaxel were analyzed by XRPD on a Bruker AXS D8 Advance Diffractometer using X-ray source—Cu Kα radiation using the wavelength 1.5418 Å and lynx Eye detector. DSC was done on a Perkin Elmer Pyris 7.0 instrument. Illustrative examples of analytical data for the non-solvated amorphous form of Cabazitaxel obtained in the Examples are set forth in the FIGS. 1-4.

In a further embodiment according to the specification, the invention also relates to a composition containing non solvated amorphous Cabazitaxel of which at least 95%, by total weight of Cabazitaxel in the composition, is the amorphous form. In yet another embodiment of the invention, the composition may be substantially free of any other known forms of Cabazitaxel solvate or any other crystalline form.

The non solvated amorphous form of Cabazitaxel (I) obtained by the process of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerin, propylene glycol or liquid paraffin.

In one embodiment of the present invention, it also includes premix comprising one or more pharmaceutically acceptable excipients in the range of 1 to 50% w/w with non solvated amorphous form of Cabazitaxel (I), while retaining the amorphous nature of the premix.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising non solvated amorphous form of Cabazitaxel of the present application include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions of non solvated amorphous form of Cabazitaxel of the present application may also comprise to include the pharmaceutically acceptable carrier used for the preparation of solid dispersion, wherever utilized in the desired dosage form preparation.

Certain specific aspects and embodiments of the present application will be explained in more detail with reference to the following examples, which are provided by way of illustration only and should not be construed as limiting the scope of the invention in any manner.

EXAMPLES

Reference Example-01

Preparation of 7,10 Dialkylated-10 DAB-III 7,10 di-methoxy-10 DAB-III used in the process of the present invention may be prepared according to the process disclosed in U.S. Pat. No. 5,962,707, wherein as per example-10, the process involves the use of Sodium hydride as base in the reaction of methyl iodide with 10-DAB-III in Tetrahydrofuran (THF) solvent. The reaction is carried out between 0-25° C. for about 7.5 hrs and subsequently pouring in diisopropyl ether (DIPE) to provide 7,10-dimethoxy-10-deacetylbaccatin with the recovery yield of more than 60%.

Also, 7, 10 di-methylation of 10 DAB-III using methyl iodide and base in the defined stoichiometry and conditions can be practiced similar to as disclosed in CN102285947A. The process involves the reaction of 10-DAB-III (20 mmol) with methyl iodide in the presence of KH (30% solution) as base (60 mmol) and THF solvent at temperature ranging between −30 to −60° C. to get the product in nearly 60% yield.

Similarly, 7, 10 di-methylation of 10 DAB-III using dimethyl sulphate and base in the defined stoichiometry and conditions can be practiced similar to as disclosed in CN102336726A (Page 12/13). The process involves the reaction of 10-DAB-III (0.1 mol) with dimethyl sulphate (0.8 mole) in the presence of KH (0.45 mole) and DMF solvent at temperature about 10° C. to provide the product 7,10 dimethoxy-10 DAB-III in nearly 99.1% purity (HPLC).

Example-01

Process for Preparation of Non-Solvated Amorphous Cabazitaxel

The process for preparation of Cabazitaxel is detailed in stepwise demonstration mentioned herein below—

STEP-A: Coupling of 7,10-Dimethoxy-10-DAB-III (a) with 3-(tert-butoxycarbonyl)-2-(4-methoxyphenyl)-4-phenyloxazolidine-5-carboxylic acid (b)

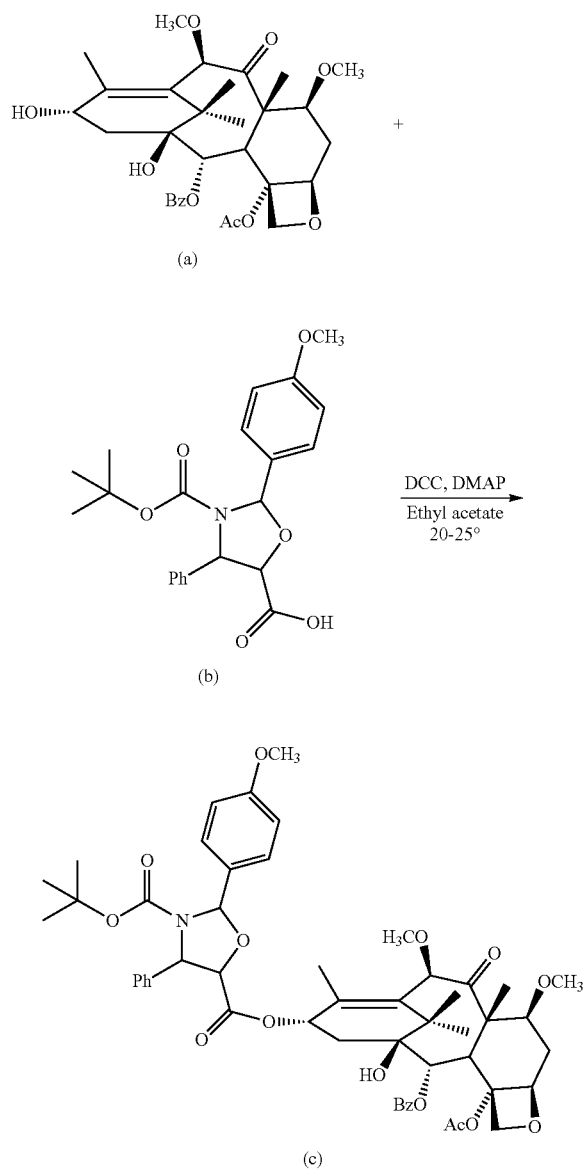

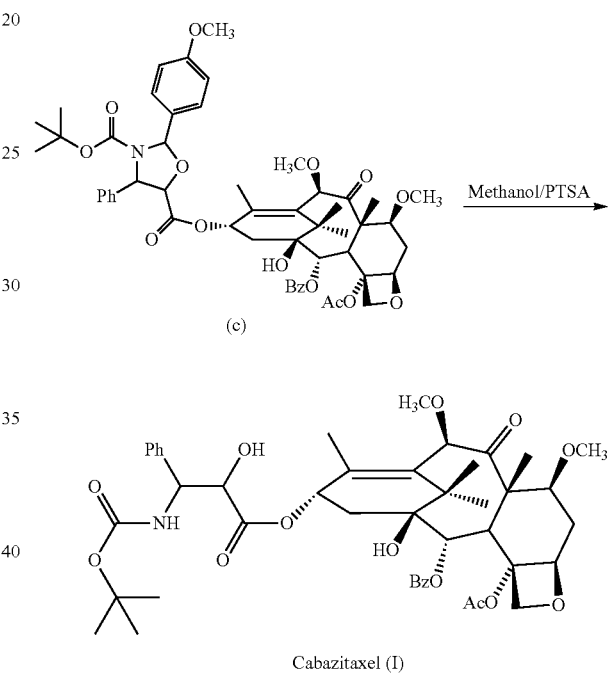

7,10-methoxy-10-deacetylbaccatin (7,10-dimethoxy-10-DAB-III) (2.5 g), 3-(tert-butoxycarbonyl)-2-(4-methoxyphenyl)-4-phenyloxazolidine-5-carboxylic acid (2.8 g, 1.6 mol) and ethyl acetate (25 mL) were charged in a single neck RB flask at room temperature (20-25° C.) under stirring. The reaction mixture was brought to 20° C. To the reaction mixture, Dicyclohexyl carbodiimide (DCC) (1.62 g, 1.8 mol), 4,4-Dimethyl aminopyridine (DMAP) (210 mg, 0.4 mol) and a small quantity of molecular sieves 4A were added under stirring conditions. The temperature of 20° C. was maintained for 24 hours. Progress of the reaction is monitored by Thin Layer Chromatography (TLC). On completion of the reaction, reaction mixture is filtered to obtain solid material. Ethyl acetate was recovered from the solid material at below 40° C. under vacuum. This material was further purified by column chromatography over silica gel (230-400 mesh). Column was packed in dichloromethane: hexane and run up to dichloromethane. When no product was observed on TLC then column was eluted with ethyl acetate: hexane to get the coupled product (c).

Yield: 1.6 g, Purity: 98.14%

Mass Spectrum: [M+1]=954.7 and [M+NH$_4^+$]=971.9

STEP-B: Ring opening of coupled product (c)

Methanol (80 mL) and coupled product (c) (1.0 g) were charged in a clean RB flask and stirred for 30 min at room temperature (RT) to get the clear solution. The reaction mixture was cooled to 0° C. under stirring, followed by addition of p-toluene sulfonic acid (PTSA) (700 mg) and further stirring for 2 hours. Reaction is continuously monitored by HPLC. Saturated NaHCO$_3$ (5.0 g in 50 mL water) solution was added at 0° C. under stirring, followed by extraction with ethyl acetate (120 mL). Organic layer was separated and the aqueous layer was extracted three times with ethyl acetate. Ethyl acetate layers were combined and made moisture free. Ethyl acetate was recovered at 40° C. under high vacuum to get the crude Cabazitaxel (I) (1.0 g, Purity: 64.69%)

STEP-C: Purification of crude Cabazitaxel.

The crude Cabazitaxel was purified by column chromatography over silica gel (230-400 mesh). Column was eluted with ethyl acetate: hexane (40:60) to get the purified Cabazitaxel.

Yield: 1.0 g, Purity: 97.54%,

Mass spectrum: [M+1]=836.8; [M+NH$_4^+$]=853.6

The obtained purified Cabazitaxel was then re-dissolved in acetone at room temperature followed by addition of hexane (25 mL) under stirring. Stirring was continued for one hour. The obtained solid was filtered and suck dried to afford 700 mg of pure Cabazitaxel (Purity: 99.18%).

STEP-D: Combining Cabazitaxel with polar organic solvent (methanol)

In a flask, Cabazitaxel (300 mg) from the above step is combined with 24 mL of methanol. Stir the reaction mass for 15-20 minutes to dissolve completely at 25-30° C. Increase the temperature of the clear solution up to 48-55° C. Maintain the temperature for 25-30 minutes.

Figure 2:
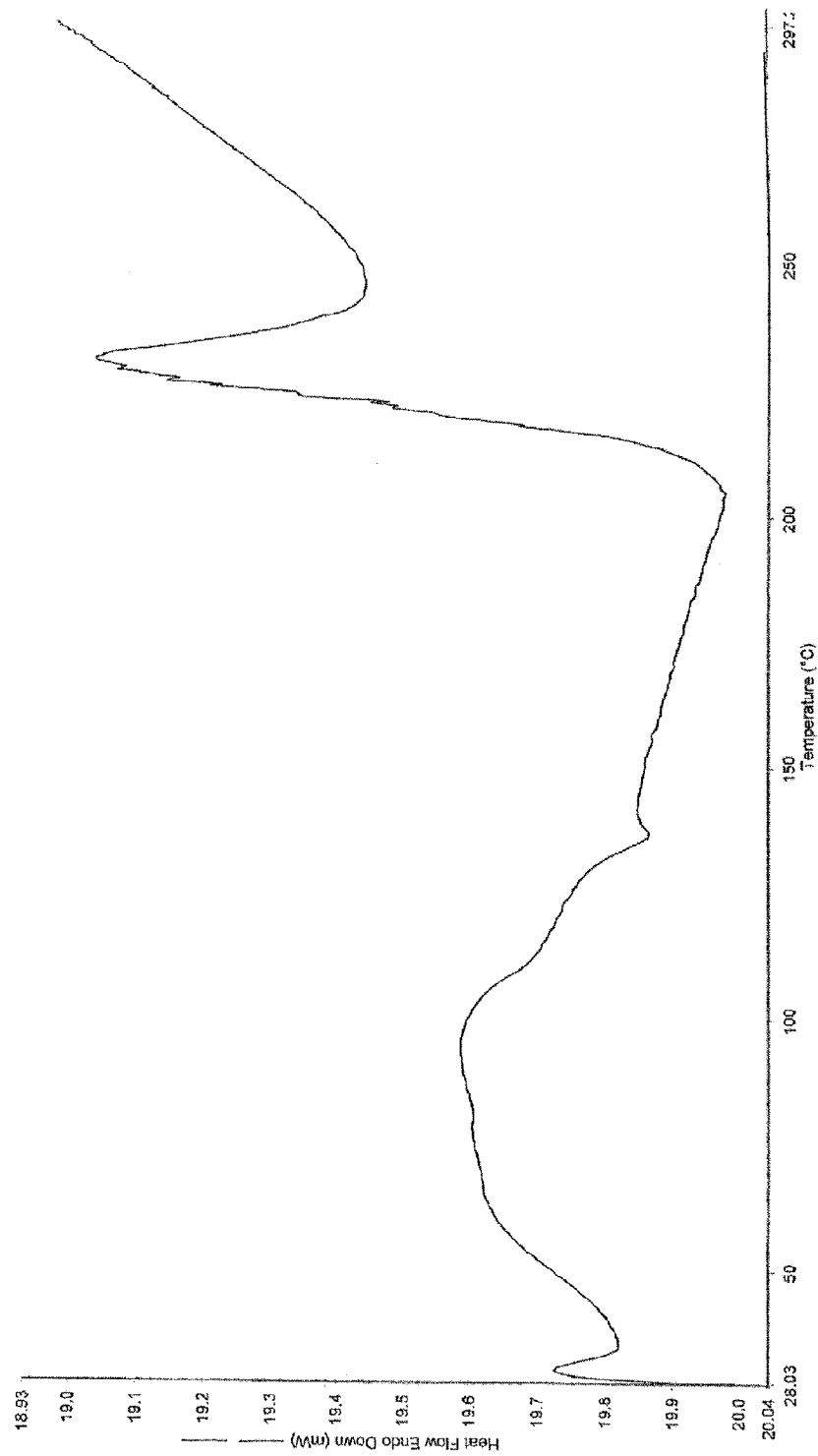
FIG. 2 is an example of a Differential Scanning calorimetry ("DSC") curve of Cabazitaxel non-solvated amorphous form.
Figure 3:
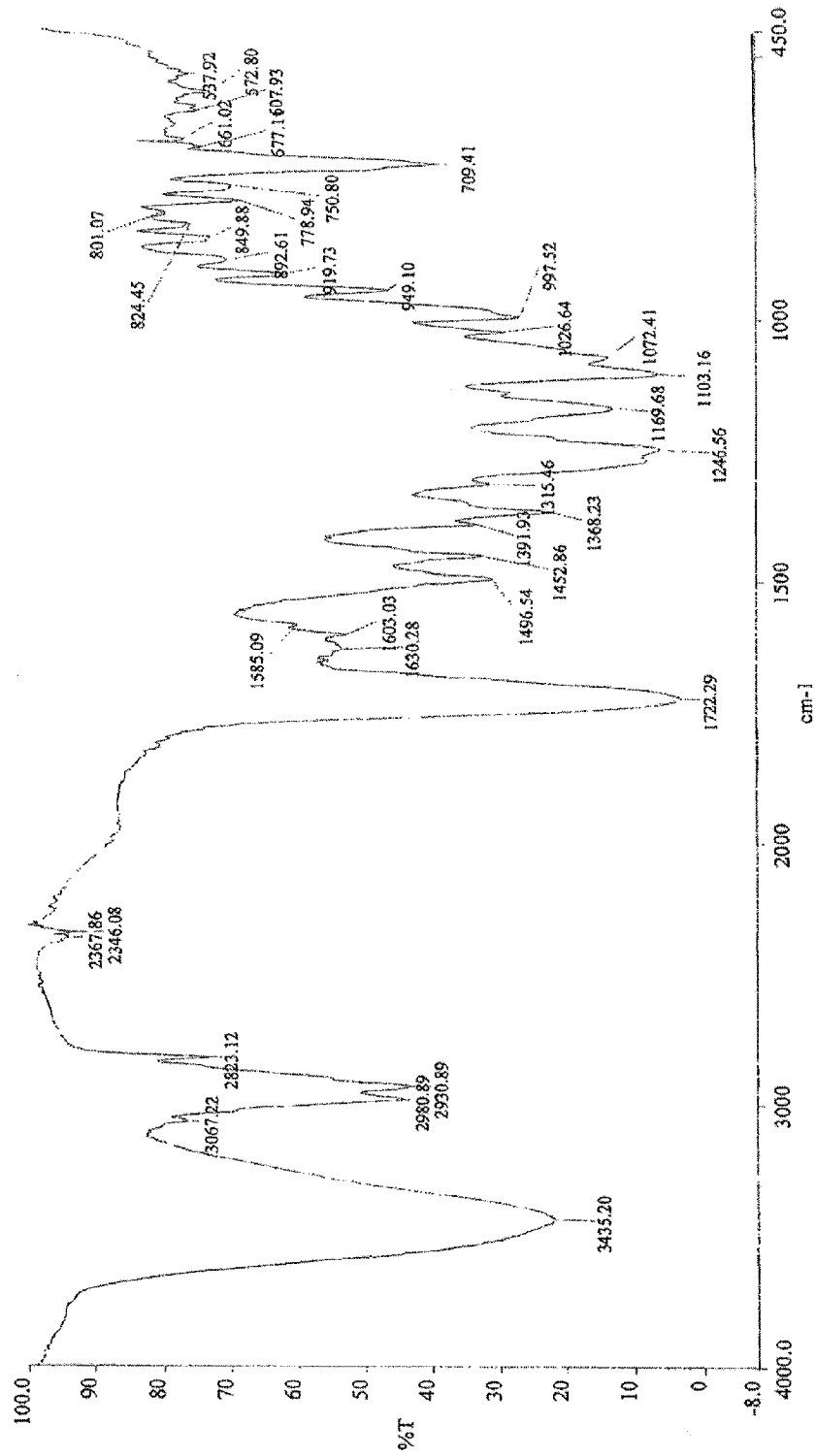
FIG. 3 is an example of IR spectral pattern of Cabazitaxel non-solvated amorphous form.

STEP-E: Recovering the solvent and isolating the non-solvated amorphous Cabazitaxel The solvent is recovered at temperature 50-55° C. under reduced pressure up to dryness to afford non-solvated amorphous Cabazitaxel, having the XRPD diffractogram, DSC and IR similar to as shown in FIGS. 1 to 3. Yield: 275 mg

Example-02

Preparation of non-solvated amorphous form of Cabazitaxel (I) by using Cabazitaxel material from any source and the polar solvent (Methanol).

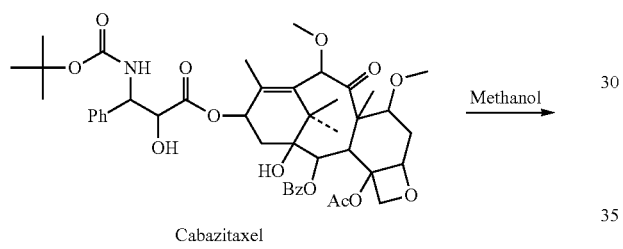

Cabazitaxel

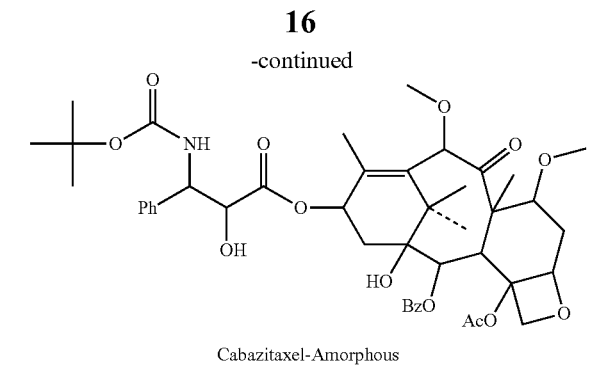

Cabazitaxel-Amorphous

Figure 4:
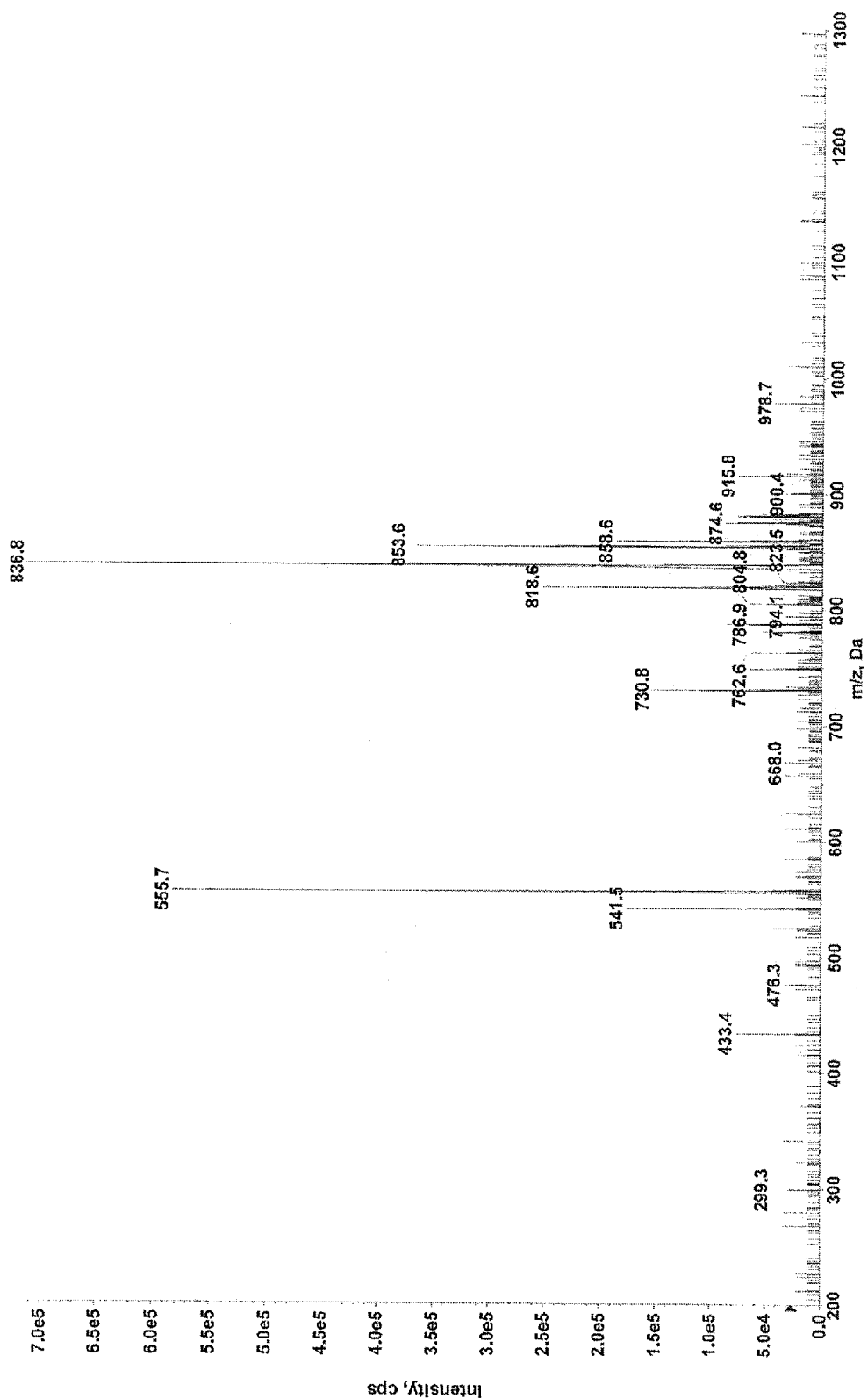
FIG. 4 is an example of a Mass spectrum of Cabazitaxel non-solvated amorphous form.

In a RB flask equipped with magnetic stirrer, thermometer and a gas bubbling tube was added Cabazitaxel (310 mg) and 25 mL of methanol. Stir the reaction mass to dissolve completely at 25-30° C. for 15-20 minutes. Raise the temperature of the clear solution up to 50-55° C. Maintain the temperature for 30 min and recover the solvent at this temperature up to dryness to afford amorphous material (280 mg) having the XRPD diffractogram, DSC and IR as shown in FIGS. 1 to 3 and Mass Spectra as shown in FIG. 4.

Mass spectrum: $[M+1]=836.8$; $[M+NH_4^+]=853.6$.

Example-03

Preparation of non-solvated amorphous form of Cabazitaxel (I) by using Cabazitaxel material from any source and the polar solvent (Methoxy ethanol).

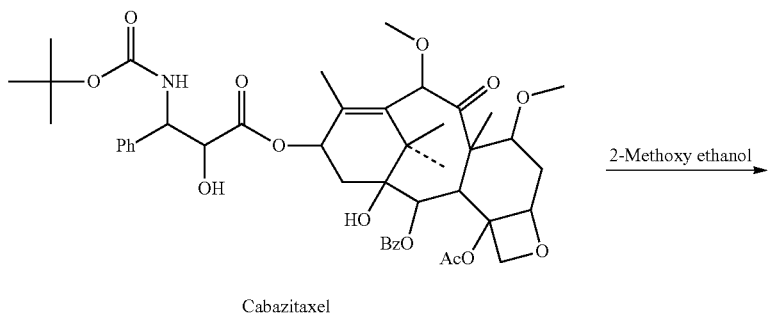

Cabazitaxel

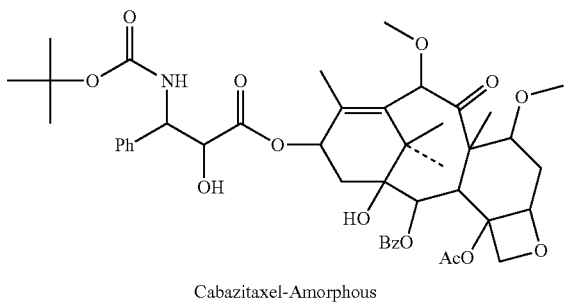

Cabazitaxel-Amorphous

To a flask equipped with magnetic stirrer, thermometer and a gas bubbling tube was added Cabazitaxel (925 mg) and 72.2 mL of 2-methoxy ethanol at temperature about 20-25° C. Stir the reaction mass to dissolve completely at same temperature. Filter the clear solution and raise the temperature of filtered reaction mass up to 45-55° C. Maintain the temperature for 1 hr and recover the solvent at this temperature up to dryness to afford amorphous material (610 mg) having the XRPD diffractogram, DSC and IR similar to as shown in FIGS. 1 to 3.

While the foregoing pages provide a detailed description of the preferred embodiments of the invention, it is to be understood that the descriptions are illustrative only of the principles of the invention and not limiting. Furthermore, as many changes can be made to the invention without departing from the scope of the invention, it is intended that all material contained herein be interpreted as illustrative of the invention and not in a limiting sense.

We claim:

1. A non-solvated amorphous form of Cabazitaxel (I),

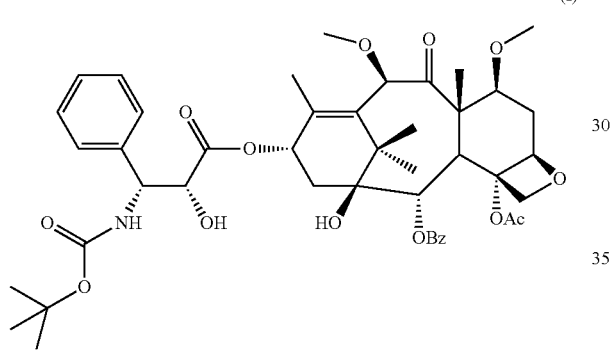

(I)

having up to 2% w/w or less of volatiles measured up to 160° C.

2. A non-solvated amorphous form of Cabazitaxel (I) having up to 2% w/w or less of volatiles measured up to 160° C. according to claim 1, wherein an XRPD is having FIG. 1 and FT-IR is having FIG. 3.

3. A process for the preparation of non-solvated amorphous form of Cabazitaxel having up to 2% w/w or less of volatiles measured up to 160° C., comprising the steps of:

i) coupling of 7,10-Dimethyl-10-DAB-III (a) with 3-(tert-butoxycarbonyl)-2-(4-methoxyphenyl)-4-phenyloxazolidine-5-carboxylic acid (b) to yield coupled product (c) in the presence of carbodiimide coupling agent;

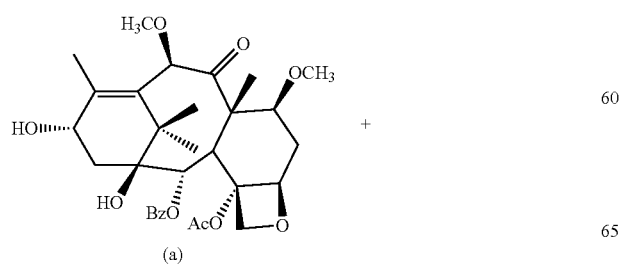

(a)

+

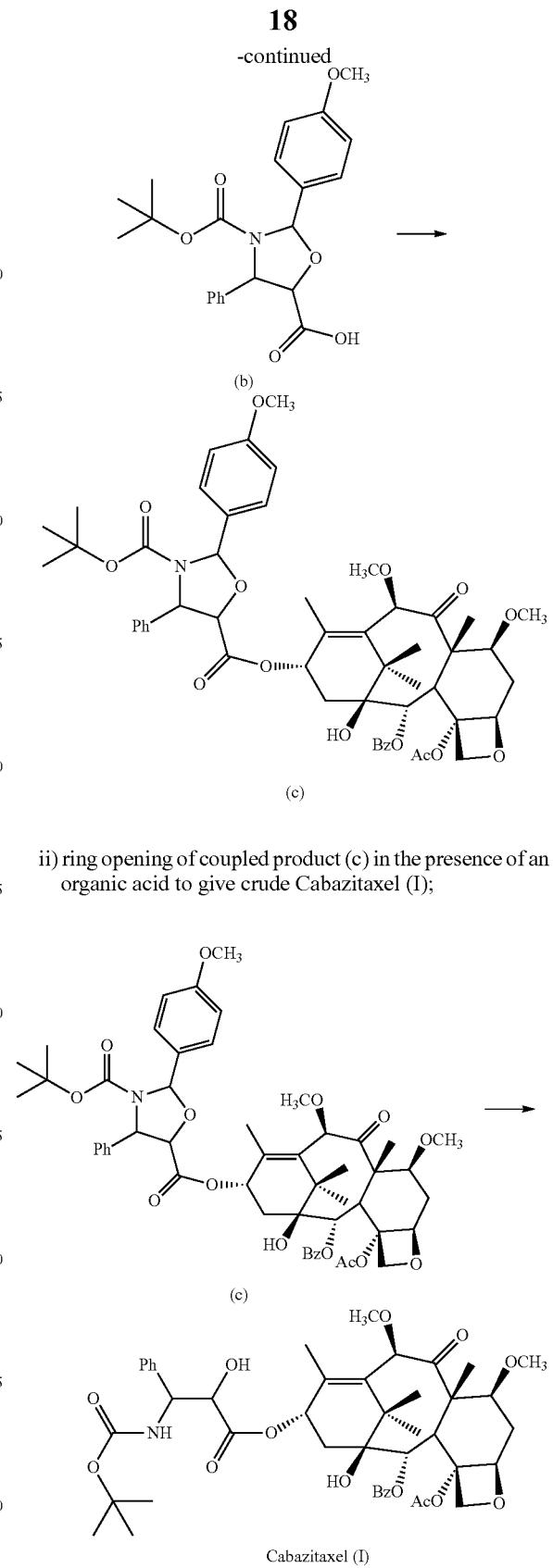

ii) ring opening of coupled product (c) in the presence of an organic acid to give crude Cabazitaxel (I);

iii) optionally purifying the Cabazitaxel of step ii);

iv) combining Cabazitaxel or reaction material of step ii) or iii) with a polar organic solvent;

v) recovering the solvent; and vi) isolating the material as non-solvated amorphous Cabazitaxel.

4. A process for preparation of non-solvated amorphous Cabazitaxel having up to 2% w/w or less of volatiles measured up to 160° C. according to claim 3, wherein organic acid used in step ii) is selected from p-toluene sulfonic acid, C2 to C5 carboxylic acid, mono or di or tri halo substituted aliphatic carboxylic acid.

5. A process for preparation of non-solvated amorphous Cabazitaxel having up to 2% w/w or less of volatiles measured up to 160° C. according to claim 3, wherein polar organic solvent used in step iv) is selected from $C_1$-$C_3$ alcohol, 2-alkoxy ethanol or dimethylsulfoxide.

6. A process for preparation of non-solvated amorphous Cabazitaxel having up to 2% w/w or less of volatiles measured up to 160° C. according to claim 5, wherein alkoxy group in 2-alkoxy ethanol solvent is comprised of alkyl group selected from C1 to C3 alkyl.

7. A process for preparation of non-solvated amorphous Cabazitaxel having up to 2% w/w or less of volatiles measured up to 160° C. according to claim 3, wherein step v) of recovering the solvent is carried out under reduced pressure and at temperature ranging between 40° C.-60° C.

8. A process for the preparation of non-solvated amorphous Cabazitaxel having up to 2% w/w or less of volatiles measured up to 160° C., characterized by XRPD pattern as per FIG. 1, from any known form of Cabazitaxel material, comprising the steps of:

i) combining Cabazitaxel or its solvate or anhydrous crystalline form with a polar organic solvent selected from methanol, 2-alkoxy ethanol, or dimethylsulfoxide;

ii) achieving dissolving of the reaction mass;

iii) recovering the solvent under reduced pressure and at temperature ranging between 40° C.-60° C.; and iv) isolating the material as non-solvated amorphous Cabazitaxel.

9. A process for the preparation of non-solvated amorphous Cabazitaxel having up to 2% w/w or less of volatiles measured up to 160° C. according to claim 8, wherein combining Cabazitaxel with a polar organic solvent in the step i) comprises dissolving at temperature ranging between 20 to 30° C.

* * * * *